United States Patent [19]

Allan et al.

[11] Patent Number: 4,477,342
[45] Date of Patent: Oct. 16, 1984

[54] APPARATUS AND METHOD FOR CONTROLLING ULTRAFILTRATION DURING HEMODIALYSIS

[75] Inventors: Jonathan M. Allan, Portland; Richard J. Burton, Tigard, both of Oreg.; Volker Jurock, Rodgau, Fed. Rep. of Germany

[73] Assignee: Becton, Dickinson and Company, Paramus, N.J.

[21] Appl. No.: 413,287

[22] Filed: Aug. 31, 1982

[51] Int. Cl.³ .............................................. B01D 31/00
[52] U.S. Cl. .................................. 210/87; 210/321.3; 210/929
[58] Field of Search ................... 210/647, 87, 96.2, 88, 210/321.3, 929

[56] References Cited

U.S. PATENT DOCUMENTS 4,267,040  5/1981  Schal ............................... 210/929 X
4,366,061  12/1982  Papanek et al. ................. 210/929 X
4,371,385  2/1983  Johnson .......................... 210/929 X

*Primary Examiner*—Frank Spear
*Attorney, Agent, or Firm*—Richard J. Rodrick

[57] ABSTRACT

Hemodialysis ultrafiltration apparatus comprises a dialyzer. A closed circuit is provided for supplying fresh dialysate to and for removing spent dialysate from the dialyzer. Blood is supplied to and removed from the dialyzer. The closed circuit for supplying fresh dialysate and removing spent dialysate is apportioned into below mean dialyzer blood pressure and above atmospheric pressure sections, with the dialyzer being positioned in the below mean dialyzer blood pressure section. A mechanism is provided for controlling the pressure of fresh dialysate introduced into the below mean dialyzer blood pressure section to substantially match the pressure on the dialysate side of the dialyzer. A mechanism is provided for controlling the above atmospheric pressure portion of the spent dialysate circuit. A pump removes spent dialysate of equivalent ultrafiltrate volume from the closed circuit to control the rate of ultrafiltrate removal from blood in the dialyzer, thus affecting the pressure on the dialysate side of the dialyzer required to sustain that rate.

A method of hemodialytic ultrafiltration is carried out substantially in accordance with the above-described apparatus.

11 Claims, 2 Drawing Figures

APPARATUS AND METHOD FOR CONTROLLING ULTRAFILTRATION DURING HEMODIALYSIS

BACKGROUND OF THE INVENTION

1. Field of the Invention.

The present invention relates to a volumetric ultrafiltration system and its method of use, and more particularly, concerns an apparatus and method for controlling ultrafiltration during hemodialysis.

2. Description of the Prior Art.

Ultrafiltration is the procedure during hemodialysis wherein excess water is removed from the blood. It is well-known to achieve satisfactory ultrafiltration by maintaining the dialysate pressure within the dialyzer lower than that of the blood pressure. During this procedure, while excess water in the blood is removable, the rate of ultrafiltration is a critical factor, since rapid removal of water from the blood may traumatically affect the patient. Various solutions to the control of the rate of ultrafiltration have been proposed, one of which is found in U.S. Pat. No. 4,021,341.

More recently, ultrafiltration control has been achieved by utilzation of a volumetric system relying upon a principle of volume conservation. One such system is described in U.S. Pat. No. 4,209,391. In the patented apparatus, a known and equal quantity of fluid is moved into and out of the dialyzer by two matched positive displacement pumps. As dialysate is moved to the dialyzer, a third pump extracts the programmed amount of dialysate from the fresh dialysate supply. The spent dialysate line demands a fixed quantity of fluid and the difference that is drawn off the fresh dialysate supply is made up by ultrafiltrate drawn across the dialyzer membrane. In U.S. Pat. No. 4,209,391, the patentees recognized that there are certain errors which arise in attempts to monitor dialysate volumes. These patentees contended that the major source of such errors is the inclusion of gases in the circulating dialysate. Based on that premise, the solution to that problem as proposed in U.S. Pat. No. 4,209,391 was to remove all gases which may enter the closed circuit in the subatmospheric pressure portion from all of the spent dialysate in order to achieve actual liquid integrity in a closed circuit.

However, in an article entitled "The Governing Equation Describing The Transient Characteristics Of Hemodialysis Ultrafiltration," by Massie, H. L., and Chen, P. I., Thirtieth ACEMB, Los Angeles, California, 5–9 Nov. 1977, page 158, the authors analyzed the process of hemodialysis specifically with respect to machine disturbances and patient blood pressure and movement. The authors concluded that dialyzer compliance is the primary source of error in the measurement of ultrafiltration, and that air displacement of fluid volume is a secondary factor. While the above-identified authors suggested an equation useful for dialysis simulation, no tangible or physical adaptation of their theory was proposed at that time. Specifically, dialyzer compliance is a reference to dialyzer membrane compliance and is a function of mean transmembrane pressure (TMP) as well as the time function change in TMP. An overall characterization of the term "compliance" is the elasticity of the closed system. Accordingly, inasmuch as the major source of error in dialysate volumetric monitoring has been shown to be the compliance factor, the hemodialysis ultrafiltration control system should be designed to account for compliance in order to accurately monitor and/or control ultrafiltration. It is to such a system that the present invention is directed in order to solve the major errors in monitoring dialysate volumes.

SUMMARY OF THE INVENTION

The hemodialysis ultrafiltration apparatus of the present invention comprises hemodialysis means. Means supplies fresh dialysate to and removes spent dialysate from the hemodialysis means. Means further supplies and removes blood from the hemodialysis means. The dialysate supplying and removing means is apportioned into below mean dialyzer blood pressure and above atmospheric pressure sections, with the hemodialysis means located in the below mean dialyzer pressure section. Means controls the pressure of fresh dialysate introduced into the below atmospheric pressure section to substantially match the pressure on the dialysate side of the hemodialysis means. Ultrafiltrate is removed from the spent dialysate means to control the rate of liquid removal from blood in the hemodialysis means.

In a preferred embodiment of this aspect of the invention, the below mean dialyzer blood pressure section includes a fresh dialysate supply line and a first portion of a spent dialysate removal line. The first positive displacement unit is in fluid communication with the fresh dialysate supply line. Each of the units includes valves and interrelated switching means. The above atmospheric pressure section of the preferred ultrafiltration apparatus includes a dialysate access line interconnected to the fresh dialysate supply line by pressure reducing means. A second portion of the spent dialysate removal line is in the above atmospheric pressure section and is interconnected to the first portion of the spent dialysate removal line by pressure increasing means. The second positive displacement unit is in fluid communication with the second portion of the spent dialysate removal line. In addition, the above atmospheric pressure section includes a dialysate drain line in fluid communication with the second portion of the dialysate removal line. Actuatable ultrafiltrate removal means is connected between the second portion of the spent dialysate line and the drain line, and is adapted to withdraw dialysate from the removal line and transfer same to the drain line. The aforementioned valves and switching means associated with the first and second positive displacement units are adapted to cause concurrently one of the units to fill with fresh dialysate as fresh dialysate is supplied to the dialyzer while the other unit fills with spent dialysate as spent dialysate is drained, and to alternate functions after the valves are reversed. Another embodiment of this aspect of the invention is to plumb the units so that concurrently one of the units fills with fresh dialysate as spent dialysate is drained while the other unit fills with spent dialysate as fresh dialysate is supplied to the dialyzer, and to alternate functions after the valves are reversed.

In a further aspect of the present invention, a method of hemodialytic ultrafiltration comprises the steps of supplying fresh dialysate to and removing spent dialysate from hemodialysis means by means apportioned into below means dialyzer blood pressure and above atmospheric pressure sections. The hemodialysis means is located in the below mean dialyzer blood pressure section. Blood is supplied to and removed from the hemodialysis means. Further, the method includes controlling the pressure of the fresh dialysate introduced into the below mean dialyzer blood pressure section to substantially match the pressure on the dialysate side of the hemodialysis means. A controlled volume of spent dialysate is removed from the fluid-tight portion of the spent dialysate circuit for controlling the rate of ultrafiltrate removal from blood in the hemodialysis means.

In accordance with the principles of the present invention, a volumetric ultrafiltration system for hemodialysis is provided in which errors due to compliance of the closed circuit system are eliminated or minimized. Stated another way, in order to achieve actual volumetric liquid integrity in a closed circuit, it is desirable to control system compliance. As alluded to above, the most significant factors in the volumetric ultrafiltration system contributing to compliant error are the dialyzer and entrained air. Accordingly, the present design, in contrast to previous ultrafiltration systems known in the prior art, emphasizes controlling the pressure of the fresh dialysate introduced into the closed circuit to match the pressure on the dialysate side of the dialyzer, thereby substantially eliminating compliance error. In addition, an embodiment of the present invention is adapted to remove gases from the incoming dialysate in order to further minimize or reduce errors in monitoring dialysate volume. Further still, the atmospheric pressure pump preferably positioned in the spent dialysate line effectively reduces the volume that the gases occupy in the closed circuit as well as place the ultrafiltrate removal means (the positive displacement pump) into a position where its performance is most accurate.

Preferably, the present invention differs from prior art ultrafiltration systems by arranging matched, commonly driven positive displacement units and a third independently driven positive displacement pump in an atmospheric pressure portion of a closed circuit which has as its boundry at each end one of the two matched positive displacement units. The positive displacement pump provides a mechanism for removing a controlled volume of spent dialysate from the fluid tight portion of the spent dialysate circuit and is positioned in the post-dialyzer region (spent dialysate) of the closed circuit in the above atmospheric pressure portion thereof. Preferably, the atmospheric pressure pump separates the positive displacement pump from the dialyzer dialysate outlet.

There are also notable distinctions between the present invention and the apparatus and method described in U.S. Pat. No. 4,209,391. Although the apparatus in the just-mentioned patent and the present apparatus preferably employ dual, commonly driven positive displacement units for the dialysate proportioning system, as well as a third independently driven positive displacement pump, the pressure apportioning and controls are significantly different between the two systems. The apparatus of U.S. Pat. No. 4,209,391 isolates the two positive displacement units from the dialyzer by means of a pressure reducer prior to the dialyzer and a positive pressure pump after the dialyzer. Accordingly, the pressures of the two piston-cylinder units are always maintained at a positive pressure, or at an above atmospheric pressure. The major contribution according to the patentees of U.S. Pat. No. 4,209,391 is the inclusion of the degassifier in the spent dialysate delivery line adjacent to the chamber of the piston-cylinder unit to be filled with spent dialysate. Moreover, the aforementioned patentees regulate the positive pressure to the post dialyzer piston-cylinder in reference to a predetermined above atmospheric pressure piston-cylinder and do not control pressure changes or fluctuations which the dialyzer may be exposed to as a result of changes to the incoming pressures. On the other hand, the present invention demonstrates the recognition that compliance serves as the major contributor to ultrafiltration measurement error. To overcome such error due to compliance, the present invention controls the supply fresh dialysate pressure so that the dialyzer perceives as close to a zero pressure change as is possible when the supply fresh dialysate is introduced into the closed circuit. In accordance with the foregoing, the present invention affords ultrafiltration control during hemodialysis on an accurate basis.

DETAILED DESCRIPTION

Figure 1:
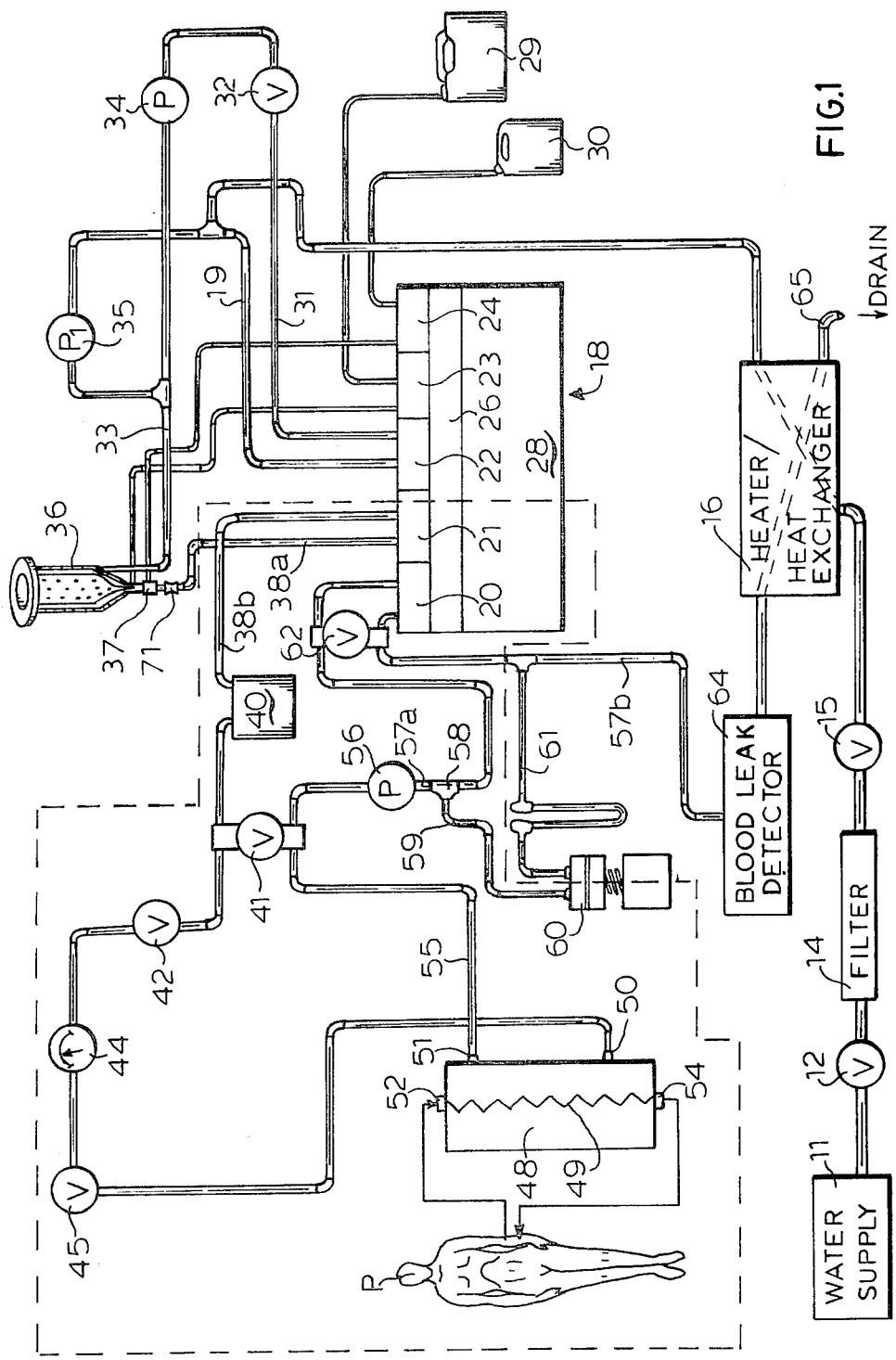
FIG. 1 is a schematic representation of the major components of the preferred apparatus of the present invention for controlling ultrafiltration during hemodialysis.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIG. 1 in particular, there is illustrated a schematic representation of the preferred apparatus 10 for controlling ultrafiltration during hemodialysis, it being understood that only the major components are represented herein, with minor components being well within the purview of one skilled in the art to ascertain. Sufficient quantities of water for the dialysis procedure are available from water supply 11 which is controlled by an on/off valve 12 in accordance with the control of the apparatus. An appropriate water filter 14 purifies the water prior to subsequent dialysis. A pressure regulator 15 monitors and controls the water pressure so that uniformity can be achieved prior to the water entering the heater and heat exchanger 16. Water is heated in the heater/heat exchanger to a temperature of 38° C. before entering the volumetric proportioning unit 18 through feedline 19. Volumetric proportioning unit 18 includes a series of valves 20, 21, 22, 23 and 24. Valves 20 are associated with the post-dialysis function; valves 21 are associated with the pre-dialysis function; valves 22 are associated with the drive function for incoming water and outgoing dialysate; valves 23 are associated with the flow of acid concentrate; and valves 24 are associated with the flow of bicarbonate concentrate. The aforementioned valves control and regulate the flow of various liquids through manifold 26 which is in fluid communication with a series of piston-cylinder units 28, all of which are part of the volumetric proportioning unit whose specific function with respect to fresh and spent dialysate will be described more completely hereinafter. Acid concentrate 29 is supplied to the volumetric proportioning unit through valves 23, whereas bicarbonate concentrate 30 is supplied to the volumetric proportioning unit through valves 24. Supply water leaves the volumetric proportioning unit through valves 22 into an air removal access line 31. Acid concentrate and bicarbonate concentrate are supplied to mix point 37 where the mixture of concentrates and the supply water result in fresh dialysate supplied to pressure reducing means 71.

Supply water passes through a flow valve 32 and also through an air removal pump 34 wherein air and other gases are driven from the water. Another pump 35 acts on the de-airified water to assist in the control of fresh dialysate pressure by the pressure reducing means 71. De-airified supply water then passes through an air trap 36 prior to entering the mix points and fresh dialysate supply line 38a. The air trap is intended to assure the removal of any entrained air in the supply water prior to mixing and the fresh dialysate re-entering the volumetric proportioning unit through valves 21. The specific proportioning and flow activities of the fresh dialysate in conjunction with the volumetric proportioning unit will be described in more detail hereinafter in conjunction with FIG. 2.

As illustrated in FIG. 1, fresh dialysate exits the volumetric proportioning unit through valves 21 into a continuation of the fresh dialysate supply line 38b. Before fresh dialysate is delivered to the dialyzer, it passes through a conductivity probe 40, by-pass valve 41 for by-passing the dialyzer, flow/by-pass fail monitor 42, flow meter 44 and pressure relief valve 45, all of which assist in the control, regulation and safety procedures for the flow of fresh dialysate into the dialyzer. A dialyzer 48 is provided and may be any of the well-known dialyzers useful for hemodialysis and including a membrane 49 therein adapted to remove waste materials and ultrafiltrate from the blood. Fresh dialysate enters the dialyzer through an inlet port 50, and after collecting waste materials and ultrafiltrate from the blood, spent dialysate exits the dialyzer through outlet port 51 and enters spent dialysate removal line 55. The hemodialyzer, of course, includes a blood inlet port 52 through which blood from a hemodialysis patient enters; a blood outlet port 54 is provided on the hemodialyzer to return blood, from which waste materials and ultrafiltrate have been removed, to the patient.

Spent dialysate is driven by pump 56 through spent dialysate line 57a which includes a branch connection 58 therein. Spent dialysate passes through branch connection 58 and enters volumetric proportioning unit 18 through valves 20. In addition, spent dialysate is removed from the spent dialysate line through branch line 59. An independently driven, positive displacement pump 60 withdraws a volume of spent dialysate from the spent dialysate line at a pre-determined and controlled rate, equivalent to the volume of ultrafiltrate to be removed from the blood, preferably electrically and automatically. By controlling the rate of withdrawal of spent dialysate from the spent dialysate removal line, the rate of ultrafiltrate removal from the blood passing through the hemodialyzer can be controlled. Spent dialysate withdrawn by the positive displacement pump is passed through line 61 which joins with the continuation of the spent dialysate removal line 57b. After spent dialysate passes through the volumetric proportioning unit it exits through valves 20 into the continuation of spent dialysate removal line 57b. A pressure release valve 62 is preferably provided in the spent dialysate removal line primarily for safety purposes; a blood leak detector 64 is also preferably provided in the spent dialysate removal line to monitor potential defects in the dailyzer membrane which would allow blood to pass into the spent dialysate rather than return to the patient. Pressure release valve 62 also provides the circuit for operation of the device in a conventional transmembrane pressure control hemodialysis procedure by control of atmospheric pressure pump 56.

After spent dialysate passes through heat exchanger 16, it is delivered into a dialysate drain line 65 which leads the spent dialysate to a drain 66, whereupon the cycle of the above described hemodialysis procedure with ultrafiltration control is completed.

Figure 2:
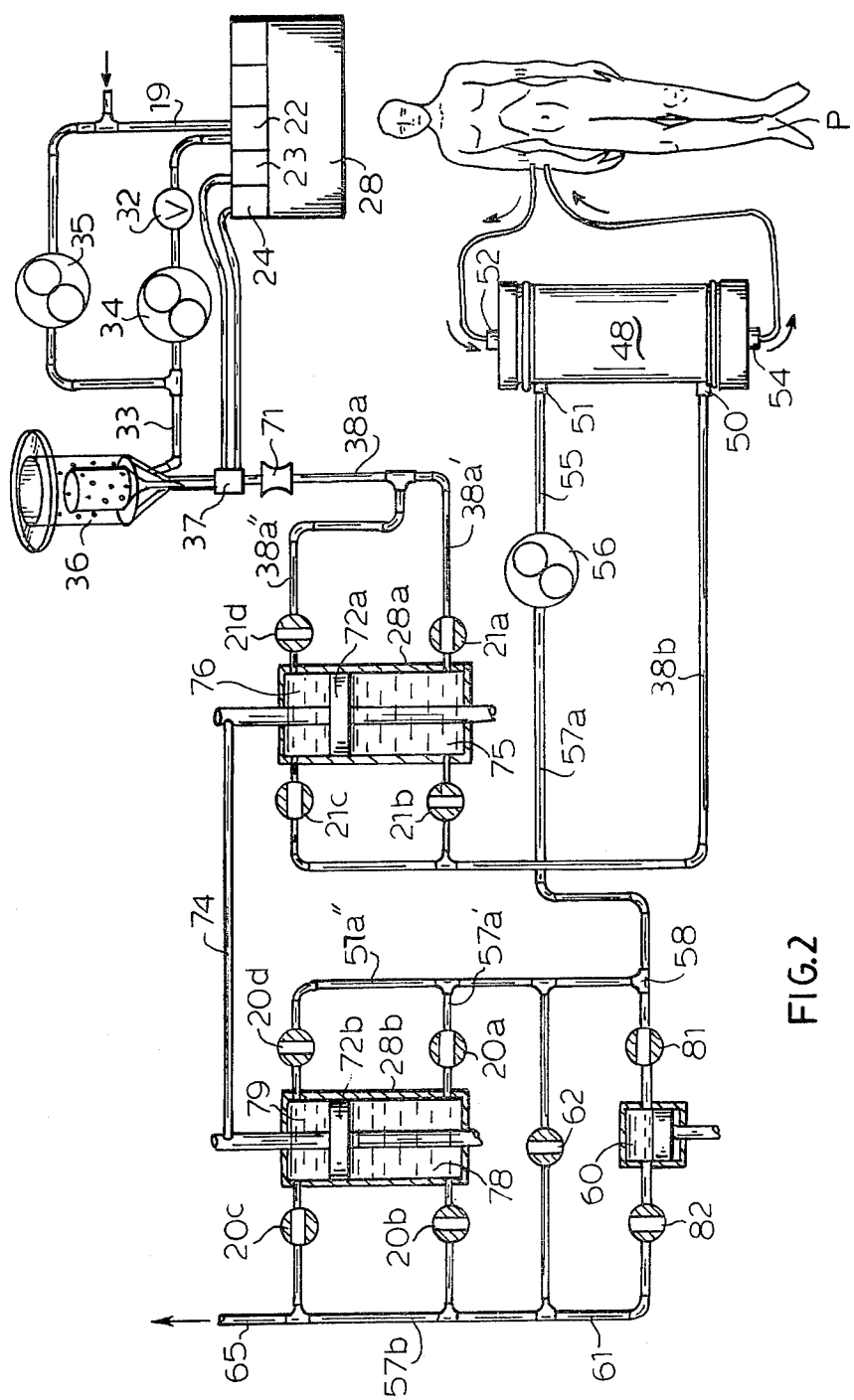
FIG. 2 is a simplified schematic illustrating the preferred closed circuit components of the apparatus of FIG. 1, indicating the below mean dialyzer blood pressure and above atmospheric sections thereof.

Referring now to FIG. 2, the simplified schematic therein illustrates the preferred closed circuit of fluid flow of the above-described apparatus. FIG. 2 depicts the fluid-tight area of the hemodialysis apparatus just described, and essentially includes those components within the dotted line area of FIG. 1. Supply water incoming through access line 33 is normally maintained at an atmospheric pressure level, due to air trap 36 acting on same. For exemplary purposes only, the pressure of deairated water in the access line may range between atmospheric (0 mm $H_g$) and positive 180 mm $H_g$. After deairated water passes through air trap 36 and the mix points 37, fluid-tightness of the closed circuit is desired. To this end, and for purposes of reducing the pressure of the fresh dialysate to that below mean dialyzer blood pressure resultant from the transmembrane pressure required to supply the volume of spent dialysate demanded by the UF pump 60, a pressure regulator 71 is provided. This pressure regulator may be nothing more than a controlled orifice or a controlled pump. This pressure regulator, while schematically illustrated adjacent air trap 36 and mix points 37, may be included anywhere in fresh dialysate supply line 38a between the air trap and valves 21 in the volumetric proportioning unit. Upon passing through pressure regulator 71, the pressure in fresh dialysate supply line is reduced to a range preferably within 0 to 10 mm $H_g$ of the required below mean dialyzer blood pressure resultant from the controlled rate of the ultrafiltration pump.

It can be seen in FIG. 2 that fresh dialysate supply line 38a bifurcates in the below mean dialyzer blood pressure region, forming two fresh dialysate supply lines, 38a' and 38a''. Fresh dialysate supply line 38a' and 38a'' are directed to positive displacement unit 28a. Positive displacement units 28a and b are preferably double acting piston-cylinder units which include a piston 72a and 72b, respectively, inside of each unit. These pistons are commonly driven by a linked-drive mechanism 74 and serve to separate each piston-cylinder unit into two chambers, i.e., chambers 75 and 76 in piston unit 28a, and chambers 78 and 79 in piston unit 28b. Each of the aforementioned chambers includes a valve associated therewith for regulating dialysate flow into and out of each chamber. These valves 20 and 21 are illustrated in FIG. 2 as ports 20a through 20d and 21a through 21d, respectively. While not illustrated in FIG. 2, both of the valves 20 and 21 are controlled by switching means, preferably electrically, so that for each pair of ports for each chamber, one port is closed, while the other port of such pair is open. Further, the switching means is designed to alternate or reverse the open and closed conditions of the aforementioned pairs of ports. The alternating position of the respective valves occurs in conjunction with the reciprocating movement of the pistons inside of the piston-cylinder units which allows the cylinder units to alternately fill one of its chambers with dialysate while the other of such chambers is emptying. This arrangement provides the volumetric proportioning of dialysate which enables the integrity of the closed circuit to be maintained for accurate control of ultrafiltration. Though illustrated as double acting piston-cylinder units, any pair of matched positive displacement units will provide the volumetric proportioning of dialysate which enables the integrity of the closed circuit to be maintained for accurate control of ultrafiltration.

Specifically, and referring to fresh dialysate supply line 38a', it can be seen that fresh dialysate enters chamber 75 through open port 21a, thereby filling chamber 75 since port 21b is closed. Piston 72a is moving upwardly as viewed in FIG. 2 so as to cause the fresh dialysate to enter chamber 75. Each positive displacement unit may receive, for example, approximately 500 ml/min. of dialysate during the operation of the apparatus being described. Inasmuch as piston 72a is moving upwardly allowing chamber 75 to fill with fresh dialysate, chamber 76 (having been previously filled with fresh dialysate) is being compressed. With valve 21d closed and valve 21c open, fresh dialysate is thus forced out of chamber 76 into fresh dialysate supply line 38b, as will be referred to hereinafter. While fresh dialysate from supply line 38a is entering piston unit 28a, the opposite is occurring in piston-cylinder 28b. Particularly, valve 20d is closed while valve 20c is open; with piston 72b moving upwardly, as viewed in FIG. 2, chamber 79 becomes compressed. Spent dialysate, previously supplied to chamber 79 when the valves were reversed, is thus forced out of that chamber into one of the spent dialysate removal lines 57b. With spent dialysate being forced out of piston unit 28b due to the upward movement of the piston therein, chamber 78 fills with spent dialysate through open valve 20a, while valve 20b remains closed. Having just explained the operation of the piston-cylinder units, it is understood that the conditions of the aforementioned chambers alternate by virtue of the reciprocative motion of the respective pistons and the operation of switching the positions of each pair of valves associated with each chamber.

Following the course of the fresh dialysate from pressure regulator 71, such fresh dialysate remains at a below mean dialyzer blood pressure level through the piston unit as it travels toward the hemodialyzer. As seen in FIG. 2, fresh dialysate supply line 38b feeds into hemodialyzer 48 at inlet port 50. Spent dialysate exits hemodialyzer 48 through outlet port 51 and enters spent dialysate removal line 55. Both the hemodialyzer and the portion of the spent dialysate removal line, segment 55, are maintained in the below mean dialyzer blood pressure section of the presently described closed fluid circuit. With the entire fresh dialysate supply line, through the respective chambers of the piston unit, the dialyzer and a segment of the spent dialysate removal line all being in the below mean dialyzer blood pressure section of the closed fluid circuit, control of system compliance is achieved. The pressure of the fresh dialysate introduced into this closed circuit is controlled to match the pressure on the dialysate side of the dialyzer (as opposed to the blood side of the dialyzer). This control and matching of the dialysate pressure permits the dialyzer to have as close to a zero change of pressure as is possible.

Positive pressure pump 56 is placed in the spent dialysate removal line to act upon the spent dialysate to increase its pressure to a level at or above that of atmospheric pressure, in the range of about 0 (atmospheric) to positive 150 mm $H_g$. The positive pressure pump also contributes to the removal of gases since it reduces the volume that the gases may occupy in the closed circuit. After passing through pump 56, the spent dialysate, now in the above atmospheric pressure section, enters the continuation of spent dialysate removal line 57a. As in the fresh dialysate line described above, spent dialysate removal line 57a bifurcates into two lines 57a' directed toward chamber 78 of piston unit 28b, and line 57a" directed toward chamber 79 of piston unit 28b. As explained above, spent dialysate enters, for example, chamber 78 in the one piston unit while being prevented from entering chamber 79. The opposite occurs when the respective valves are reversed in accordance with the switching mechanism built into the apparatus. Spent dialysate passing through the respective piston unit enters a continuation of spent dialysate removal line 57b which is in fluid communication with dialysate drain line 65 through which spent dialysate is drained. Spent dialysate removal line 57b, as well as drain line 65, is maintained at an above atmospheric pressure level consistent with the back pressure of the heat exchanger and drain line.

Spent dialysate is withdrawn from spent dialysate removal line 57a through branching connection 58, whereupon the withdrawn spent dialysate travels through line 59. As described above, ultrafiltrate pump 60 operates to remove a measured volume of spent dialysate from the spent dialysate removal line. Pump 60 is preferably driven independently from driving mechanism 74 associated with the driving function of the piston units. Mbreover, it is preferred that pump 60 be a positive displacement pump. Anothger embodiment of this aspect of this invention may be a pump coupled with a flow measurement device. Independent control of the desired quantity of spent dialysate to be withdrawn demands an equal quantity of ultrafiltrate removal from the blood in the hemodialyzer due to the fluid tight integrity of the closed system. Due to the tight hydralic quality of the closed circuit and the volumetric accuracy of the matched positive displacement units 28a and 28b of the present invention, when pump 60 is not operating and valve 81 is closed, there is no resultant ultrafiltration. In this regard, ultrafiltration is controlled through the actuation of pump 60; further, operation of pump 60 and valves 81 and 82 allow the quantity of dialysate removed from the spent dialysate removal line to be appropriately varied. Spent dialysate of equivalent ultrafiltrate volume withdrawn by virtue of pump 60 then travels into removal line 61 which communicates with the continuation of spent dialysate removal line 57b for eventual draining.

Another branch of spent dialysate removal line 57a includes pressure relief valve 62 therein to safely regulate the eventuality of excess pressures. Valve 62 also provides the mechanism for operation of this invention in a conventional TMP control hemodialysis procedure by control of atmospheric pressure pump 56.

In accordance with the foregoing apparatus and process, the withdrawal of spent dialysate from the fluid circuit controls the rate and quantity of water removal from blood in the hemodialyzer, thereby achieving ultrafiltration. Accuracies are also achieved and improved by virtue of the volumetric proportioning approach utilized by the present invention, and the matching of pressure on the fresh dialysate line prior to the inlet piston units with the pressure on the dialysate side of the hemodialyzer. This matching of pressures effectively controls and negates system compliance, attributed most significantly to the dialyzer and entrained gases, and therefore enhances accuracy since compliance has been deemed to be the primary source of error in the measurement of ultrafiltration.

What is claimed is:

1. An apparatus for controlling ultrafiltration during hemodialysis having below mean dialyzer blood pressure and above atmospheric pressure sections, said below mean dialyzer blood pressure section comprising:

a fresh dialysate supply line and a first portion of a spent dialysate removal line;

a pair of matched positive displacement units each including valves and interrelated switching means, the first of said units being interconnected to said supply line by a mix point and pressure reducing means; and a hemodialyzer for the dialysis and ultrafiltration of blood including inlet and outlet blood ports, an inlet dialysate port for the entry of fresh dialysate and an outlet dialysate port for the exit of spent dialysate; said above atmospheric pressure section comprising:

a second portion of the spent dialysate removal line interconnected to said first portion of said spent dialysate removal line by pressure increasing means;

the second of said positive displacement units being in fluid communication with the second portion of said spent dialysate removal line;

a dialysate drain line in fluid communication with the second portion of said dialysate removal line; and ultrafiltrate removal means connected between the second portion of said spent dialysate line and said drain line adapted to withdraw dialysate from said removal line and transfer same to said drain line;

said valves and switching means adapted to cause concurrently one of said units to fill with fresh dialysate as fresh dialysate is supplied to said dialyzer while the other unit fills with spent dialysate as spent dialysate is drained and to alternate functions after said valves are reversed.

2. The apparatus of claim 1 wherein the entire fresh dialysate supply line is in said below atmospheric pressure section.

3. The apparatus of claim 1 wherein said means for separating in each unit is a double-acting piston which moves reciprocatively inside each of said units.

4. The apparatus of claim 1 wherein said pressure reducing means is a controlled orifice.

5. The apparatus of claim 1 wherein said pressure reducing means is a controlled pump.

6. The apparatus of claim 1 wherein said pressure increasing means is a pump.

7. The apparatus of claim 1 wherein said actuatable ultrafiltrate removal means is a positive displacement unit.

8. The apparatus of claim 1 wherein said actuatable ultrafiltrate removal means is a pump and a flow measurement apparatus.

9. The apparatus of claim 1 which further includes a degassifier located in the dialysate access line adjacent to said pressure reducing means.

10. The apparatus of claim 1 which further includes means for actuating said ultrafiltrate removal means independently of the means adapted to fill said matched first and second positive displacement units.

11. The apparatus of claim 10 wherein said means for actuating is controllable to vary the quantity of dialysate transferred.

* * * * *